(12) United States Patent
Antrim

(10) Patent No.: US 6,803,459 B2
(45) Date of Patent: Oct. 12, 2004

(54) BRANCHED STARCHES AND BRANCHED STARCH HYDROLYZATES

(75) Inventor: Richard L. Antrim, Solon, IA (US)

(73) Assignee: Grain Processing Corporation, Muscatine, IA (US)

(*) Notice: Subject to any disclaimer, the term of this patent is extended or adjusted under 35 U.S.C. 154(b) by 0 days.

(21) Appl. No.: 10/226,809

(22) Filed: Aug. 23, 2002

(65) Prior Publication Data

US 2003/0005922 A1 Jan. 9, 2003

Related U.S. Application Data

(63) Continuation of application No. 09/725,990, filed on Nov. 29, 2000.
(60) Provisional application No. 60/168,785, filed on Dec. 2, 1999.

(51) Int. Cl.$^7$ ................................................. C08B 30/00
(52) U.S. Cl. ........................ 536/102; 536/1.11; 536/4.1; 536/45; 536/123.1

(58) Field of Search ................................. 536/102, 1.11, 536/4.1, 123.1, 45; 514/60; 426/48, 52

(56) References Cited

U.S. PATENT DOCUMENTS

| 3,974,032 A | * | 8/1976 | Harjes et al. | ................. 195/31 |
| 4,454,161 A | * | 6/1984 | Okada et al. | ................. 426/48 |
| 5,904,941 A | * | 5/1999 | Xu et al. | ....................... 426/52 |

* cited by examiner

*Primary Examiner*—James O. Wilson
*Assistant Examiner*—Ganapathy Krishnan
(74) *Attorney, Agent, or Firm*—Banner & Witcoff, Ltd.

(57) ABSTRACT

The present invention provides a starch that includes at least one glucose polymer having greater than 4% alpha 1-6 glycosidic linkages. The present invention further provides a starch hydrolyzate that includes at least one glucose oligomer having greater than 4% alpha 1-6 glycosidic linkages. The starch and starch hydrolyzate present invention have improved aqueous solution stability and are less likely to retrograde than are solutions of unbranched linear starches or starch hydrolyzates.

8 Claims, No Drawings

BRANCHED STARCHES AND BRANCHED STARCH HYDROLYZATES

CROSS-REFERENCE TO RELATED PATENT APPLICATIONS

This patent application claims priority to provisional U.S. Patent Application No. 60/168,785, filed on Dec. 2, 1999.

TECHNICAL FIELD OF THE INVENTION

This invention relates to novel branched starch and starch hydrolyzates, solutions thereof, and methods of making and using them.

BACKGROUND OF THE INVENTION

The molecular structure and origins of starch are well documented in the literature. Starch from plant sources typically exists in two forms, amylose and amylopectin. Amylose is a linear polymer of glucose linked by alpha 1–4 glycosidic bonds. Amylopectin is a branched polymer of glucose containing up to 4% alpha 1–6 glycosidic bonds and about 96% alpha 1–4 glycosidic bonds. It is the 1–6 bonds which create the branches in an otherwise linear polymer. Starch normally is found in nature as a mixture of about 25% amylose and 75% amylopectin. So called waxy varieties of plants exist which contain up to 100% amylopectin. Corn processed by the corn processing industry is, for the most part, dent corn, although small amounts of waxy or a high amylose variety are also processed into specialty products.

Amylose molecules or partial hydrolyzates thereof, because they are linear tend to associate through hydrogen bonding with themselves and with other amylose molecules to form essentially water-insoluble aggregates. The process of insolubilization is usually termed retrogradation. This phenomenon is problematic in the starch processing industry in that it causes processing difficulties in the production of carbohydrate products from starch. Perhaps more importantly, retrogradation phenomena cause defects in product quality, such as hazing, precipitation and clouding in solutions of the carbohydrates. Stable solutions of carbohydrates are deemed desirable in the industry.

As such, there is a need for new carbohydrates that form stable aqueous solutions as well as a need for a method of treating linear carbohydrates so as to overcome the retrogradation problems associated therewith. The present invention provides such carbohydrates and methods. These and other advantages of the present invention, as well as additional inventive features, will be apparent from the description of the invention provided herein.

THE INVENTION

The present invention provides a starch that includes at least one glucose polymer having greater than 4% alpha 1–6 glycosidic linkages. The present invention further provides a starch hydrolyzate that includes at least one glucose-oligomer having greater than 4% alpha 1–6 glycosidic linkages. The starch and starch hydrolyzate of the present invention provide stable aqueous solutions that would not be attainable with unbranched linear poly- or oligo-saccharides. In this regard, the present invention provides a stable aqueous starch solution that includes one or more amylose molecules that are branched by one or more alpha 1–6 glycosidic linkages. The present invention also provides a stable aqueous starch hydrolyzate solution that includes one or more amylose hydrolyzate molecules that are branched by one or more alpha 1–6 glycosidic linkages.

The present invention further provides a method of improving the aqueous solution stability of a starch that contains amylose molecules, which method includes introducing one or more alpha 1–6 glycosidic linkages so as to branch one or more of the amylose molecules in the starch. The method of the present invention also can be applied to starch hydrolyzates, preferably those that contain amylose hydrolyzates. In this regard, the present invention provides a method of improving the aqueous solution stability of a starch hydrolyzate, which method includes introducing one or more alpha 1–6 glycosidic linkages so as to branch one or more of the amylose hydrolyzate molecules in the starch hydrolyzate.

The method of the present invention similarly applies to amylose and amylose hydrolyzates. In this respect, the present invention provides a method of improving the aqueous solution stability of amylose by introducing one or more alpha 1–6 glycosidic linkages so as to branch one or more of the amylose molecules. The present invention also provides a method of improving the aqueous solution stability of an amylose hydrolyzate by introducing one or more alpha 1–6 glycosidic linkages so as to branch one or more amylose hydrolyzate molecules.

DESCRIPTION OF THE INVENTION

The present invention is predicated on the discovery that starch branching enzymes derived from, for example, corn, rice or potato, or produced from microbes as a result of a cloned plant gene, when used to treat starches or starch hydrolyzates such as malto-oligosaccharides can significantly improve the properties of starches or starch hydrolyzates such as malto-oligosaccharides. By treatment of the starches or starch hydrolyzates, $\alpha$ 1–6 branch points are introduced. Up to 10% or even higher of the glycosidic bonds can be provided as $\alpha$ 1–6 bonds (i.e., alpha 1–6 bonds). The starches or starch hydrolyzates so treated can be derived for any number of sources, such as corn, wheat, barley, rice, and the like. Starch hydrolyzates are described, for example, in U.S. Pat. Nos. 6,613,898, 6,380,379 and 60/139,184, now expired and in International Patent Application No. PCT/US99/01098, all of which are incorporated herein by reference.

By introduction of additional branch points in starches or starch hydrolyzates over those naturally occurring in the amylopectin fraction of starch, a number of functional properties of commercial importance are greatly improved. Also, new useful functional properties are provided. For example, the branched species are more stable in solution resulting in reduced tendency to haze or precipitate. The branched species exhibit novel and useful function properties such as viscosity, higher achievable solution concentrations, flowability, coating behavior, solution thickening behavior and film-forming properties. Physiological properties such as rate of caloric release or glycemic response are improved, opening opportunities for use in nutraceutical products. Although applicant does not wish to be bound by any one particular theory, it is believed that the branches introduced to the starch or starch hydrolyzate of the present invention interfere with the inter- or intra-molecular association of molecules that would otherwise promote retrogradation.

Enzymes known as starch branching enzymes exist in all plants that contain amylopectin starch, and function in nature to create $\alpha$ 1–6 branches during synthesis of starch in the plant. These enzymes, although known to starch scientists for years, have not been seriously considered for commercial use because they occurred in minute amounts in plants and were not produced commercially. Although the branching enzymes are still not produced commercially today, the potential exists for commercial and inexpensive production as a result of modern methods of DNA cloning whereby a gene from a plant such as corn, rice or potato coding for synthesis of starch branching enzyme can be cloned into microbes. Most enzymes used for commercial conversion of starch today are produced by large-scale microbial fermentation.

Accordingly, the present invention provides a starch that includes at least one glucose polymer having greater than 4% alpha 1–6 glycosidic linkages. The number of alpha 1–6 glycosidic linkages in the starch of the present invention exceeds that of even pure amylopectin. The starch of the present invention preferably includes a glucose polymer having greater than about 5% alpha 1–6 glycosidic linkages, but more preferably includes a glucose polymer having greater than about 6% alpha 1–6 glycosidic linkages. Most preferably, the starch of the present invention includes a glucose polymer having greater than about 7% alpha 1–6 glycosidic linkages, for example, from about 8% to about 10% alpha 1–6 glycosidic linkages, or even greater than 10% alpha 1–6 glycosidic linkages.

The present invention further provides a starch hydrolyzate that includes at least one glucose oligomer having greater than 4% alpha 1–6 glycosidic linkages. It will be appreciated that the branched starch hydrolyzates of the present invention include branched partial starch hydrolyzates. The number of alpha 1–6 glycosidic linkages in the starch of the present invention exceeds the number of such linkages that can be obtained even from hydrolyzates of pure amylopectin.

The starch hydrolyzate of the present invention preferably includes a glucose oligomer having greater than about 5% alpha 1–6 glycosidic linkages, but more preferably includes a glucose oligomer having greater than about 6% alpha 1–6 glycosidic linkages. Most preferably, the starch hydrolyzate of the present invention preferably includes a glucose oligomer having greater than about 7% alpha 1–6 glycosidic linkages, for example, from about 8% to about 10% alpha 1–6 glycosidic linkages, or even greater than 10% alpha 1–6 glycosidic linkages.

The starch of the present invention provides a stable aqueous solution that overcomes retrogradation problems typically associated with linear unbranched starch molecules. In this regard, the present invention provides a stable aqueous starch solution that includes one or more amylose molecules that are branched via one or more alpha 1–6 glycosidic linkages. Preferably, the amylose in the starch solution of the present invention contains at least about 4% alpha 1–6 glycosidic linkages, but more preferably contains at least about 5% alpha 1–6 glycosidic linkages, and still more preferably contains at least about 6% alpha 1–6 glycosidic linkages. Most preferably, the amylose in the starch solution of the present invention contains at least about 7% alpha 1–6 glycosidic linkages, for example, from about 8% to about 10% alpha 1–6 glycosidic linkages, or even greater than 10% alpha 1–6 glycosidic linkages.

The starch hydrolyzate of the present invention also provides a stable aqueous solution that overcomes retrogradation problems that can be associated with certain unbranched linear starch hydrolyzate molecules. In this regard, the present invention provides a stable aqueous starch hydrolyzate solution that includes one or more amylose hydrolyzate molecules that are branched via one or more alpha 1–6 glycosidic linkages. Preferably, the amylose hydrolyzate in the starch hydrolyzate solution of the present invention contains at least about 4% alpha 1–6 glycosidic linkages, but more preferably contains at least about 5% alpha 1–6 glycosidic linkages, and still more preferably contains at least about 6% alpha 1–6 glycosidic linkages. Most preferably, the amylose hydrolyzate in the starch hydrolyzate solution of the present invention contains at least about 7% alpha 1–6 glycosidic linkages, for example, from about 8% to about 10% alpha 1–6 glycosidic linkages, or even greater than 10% alpha 1–6 glycosidic linkages.

The present invention further provides methods of improving the aqueous solution stability of starch and hydrolyzates thereof. In particular, the present invention provides a method of improving the aqueous solution stability of a starch that contains amylose molecules, which method includes introducing one or more alpha 1–6 glycosidic linkages so as to branch one or more of the amylose molecules in the starch. The present invention also provide a method of improving the aqueous solution stability of a starch hydrolyzate that contains amylose hydrolyzate molecules, which method includes introducing one or more alpha 1–6 glycosidic linkages so as to branch one or more of the amylose hydrolyzate molecules in the starch hydrolyzate.

The method of the present invention likewise can be applied to a method of improving the solution stability of amylose. Thus, in another embodiment the present invention provides a method of improving the aqueous solution stability of amylose, which method includes introducing one or more alpha 1–6 glycosidic linkages so as to branch one or more of the amylose molecules. The method of the present invention applies to hydrolyzates of amylose. In this respect, the present invention provides a method of improving the aqueous solution stability of an amylose hydrolyzate, which method includes introducing one or more alpha 1–6 glycosidic linkages so as to branch one or more molecules of the amylose hydrolyzate.

The following examples further illustrate the present invention but, of course, should not be construed as in any way limiting its scope.

EXAMPLE

This example illustrates the preparation of a branched starch hydrolyzate of the present invention.

A slurry of dent corn starch in water at about 30% solids is partially hydrolyzed with alpha amylase to form a solution of malto-oligosaccharides. The DE of the solution is about 10. Either during the alpha amylase hydrolysis or subsequent to the hydrolysis about 50 IU of branching enzyme is added to the starch mixture and held for 4 hours at pH 6, and a temperature of 40° C. A portion of the treated starch is concentrated to a syrup, and another portion is spray dried. The alpha amylase is obtained from Genencor International, Inc. The branching enzyme is obtained from sweet corn endosperm by water extraction of the ground endosperm and isolation of active fractions resulting from chromatography on a column of DEAE-cellulose. Compared to control solutions of malto-oligosaccharides, which are not treated with branching enzyme, the solutions resulting from treatment are stable against hazing upon storage. Spray dried malto-oligosaccharides which are treated with branching enzyme, when dissolved in water, form solutions which are clear and stable against hazing compared to non-treated controls.

While particular embodiments of the invention have been shown, it will be understood that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention.

What is claimed is:

1. A spray dried starch comprising at least one glucose polymer having greater than 4% alpha 1–6 glycosidic linkages.

2. The starch of claim 1, comprising a glucose polymer having greater than about 5% alpha 1–6 glycosidic linkages.

3. The starch of claim 1, comprising a glucose polymer having greater than about 6% alpha 1–6 glycosidic linkages.

4. The starch of claim 1, comprising a glucose polymer having greater than about 7% alpha 1–6 glycosidic linkages.

5. A spray dried starch hydrolyzate comprising at least one glucose oligomer having greater than 4% alpha 1–6 glycosidic linkages, said starch hydrolyzate comprising a maltoogliosaccharide.

6. The starch hydrolyzate of claim 5, comprising a glucose oligomer having greater than about 5% alpha 1–6 glycosidic linkages, said starch hydrolyzate comprising a maltoogliosaccharide.

7. The starch hydrolyzate of claim 5, comprising a glucose oligomer having greater than about 6% alpha 1–6 glycosidic linkages, said starch hydrolyzate comprising a maltoogliosaccharide.

8. The starch hydrolyzate of claim 5, comprising a glucose oligomer having greater than about 7% alpha 1–6 glycosidic linkages, said starch hydrolyzate comprising a maltoogliosaccharide.

* * * * *